(12) United States Patent
Yin et al.

(10) Patent No.: US 12,075,787 B2
(45) Date of Patent: Sep. 3, 2024

(54) **USE OF APPLICATION MODE OF *TRICHODERMA HARZIANUM* (*T. HARZIANUM*) IN GROWTH AND INDUCED RESISTANCE OF *NICOTIANA TABACUM* (*N. TABACUM*)**

(71) Applicant: HENAN AGRICULTURAL UNIVERSITY, Zhengzhou (CN)

(72) Inventors: Quanyu Yin, Zhengzhou (CN); Zhihao Kuang, Zhengzhou (CN); Xinfa Wang, Zhengzhou (CN); Guoshun Liu, Zhengzhou (CN)

(73) Assignee: HENAN AGRICULTURAL UNIVERSITY, Zhengzhou (CN)

( * ) Notice: Subject to any disclaimer, the term of this patent is extended or adjusted under 35 U.S.C. 154(b) by 0 days.

(21) Appl. No.: 18/281,326

(22) PCT Filed: Dec. 29, 2022

(86) PCT No.: PCT/CN2022/143323
§ 371 (c)(1),
(2) Date: Sep. 11, 2023

(87) PCT Pub. No.: WO2023/202153
PCT Pub. Date: Oct. 26, 2023

(65) Prior Publication Data
US 2024/0081342 A1    Mar. 14, 2024

(30) Foreign Application Priority Data

Apr. 18, 2022  (CN) .......................... 202210401137.2

(51) Int. Cl.
| | | |
|---|---|---|
| *A01N 63/38* | (2020.01) | |
| *A01P 3/00* | (2006.01) | |
| *A01P 21/00* | (2006.01) | |
| *C12N 1/14* | (2006.01) | |
| *C12R 1/885* | (2006.01) | |

(52) U.S. Cl.
CPC ............... *A01N 63/38* (2020.01); *A01P 3/00* (2021.08); *A01P 21/00* (2021.08); *C12N 1/14* (2013.01); *C12R 2001/885* (2021.05)

(58) Field of Classification Search
CPC . A01N 63/38; A01P 21/00; A01P 3/00; C12N 1/14; C12R 2100/885
See application file for complete search history.

(56) References Cited

U.S. PATENT DOCUMENTS 4,477,433 A  *  10/1984  Hultman .................. C05F 9/04
                                                        435/256.7
2021/0329857 A1    10/2021  Fang et al.

FOREIGN PATENT DOCUMENTS

| CN | 103146586 A | 6/2013 |
|---|---|---|
| CN | 104291892 A | 1/2015 |
| CN | 113966704 A | 1/2022 |
| CN | 114847114 A | 8/2022 |
| KR | 20160045476 A | 4/2016 |

OTHER PUBLICATIONS

Wei Qu, et al., Effects of Trichoderma harzianum strain WY-1 on growth and disease control of tomato, Jiangsu Agricultural Sciences, 2018, pp. 94-96, vol. 46, No. 5.
Wang Yichun, et al., Effects of Application Modes of Trichoderma on Seedling Quality Characteristics of Cucumber and Control Effect against Fusarium Wilt, Chinese Journal of Biological Control, 2019, pp. 416-425, vol. 35, No. 3.
Hongjiang Zhu, Study on the activity and mechanism of Trichoderma harzianum TMN-1 inducing tobacco bacterial wilt resistance, Southwest University Master's Thesis, China Academic Journal Electronic Publishing House, 2020, pp. 1-83.
Meiyun Li, et al., Cultural Characteristics of Trichoderma harzianum and its Inhibition to Phytophthora nicotianae, Microbiology Bulletin, 2006, pp. 79-83, vol. 33, No. 6.

* cited by examiner

*Primary Examiner* — Ali Soroush
(74) *Attorney, Agent, or Firm* — Bayramoglu Law Offices

(57) ABSTRACT

A use of an application mode of *Trichoderma harzianum* (*T. harzianum*) in growth and induced resistance of *Nicotiana tabacum* (*N. tabacum*) includes the following specific operation steps: S1. experimental materials: preparation of test media and bacterial solutions; S2. experimental treatments: S2.1 control treatment; S2.2 seed soaking treatment; S2.3 root irrigation treatment; and S2.4 foliar inoculation treatment; S3. test determination indexes and methods: S3.1 determination of biological traits; S3.2 determination of physiological and biochemical indexes; and S3.3 determination of disease resistance and induced resistance indexes; and S4. data processing: subjecting data to a difference significance test. Different application modes of *T. harzianum* all can promote the growth of *N. tabacum* plants and reduce the occurrence of tobacco black shank (TBS), among which a root irrigation treatment at a transplanting stage leads to an optimal effect.

3 Claims, 4 Drawing Sheets

FIG. 1

| Treatment | Plant height/cm | | Stem circumference/cm | | Leaf area/cm² | |
|---|---|---|---|---|---|---|
| | Measured value | ΔCK/% | Measured value | ΔCK/% | Measured value | ΔCK/% |
| Control | 31.65 ± 1.62 d | - | 3.29 ± 0.32 b | - | 238.03 ± 13.12 c | - |
| Seed soaking | 44.26 ± 3.22 b | 39.84 | 3.77 ± 0.34 a | 14.59 | 336.93 ± 24.20 b | 41.55 |
| Root irrigation | 48.81 ± 2.85 a | 54.21 | 3.85 ± 0.39 a | 17.02 | 398.52 ± 25.61 a | 67.42 |
| Foliar spraying | 39.27 ± 2.39 c | 24.08 | 4.06 ± 0.45 a | 23.40 | 315.18 ± 17.29 b | 32.41 |

FIG. 2

| Treatment | Total root length/cm | | Root surface area/cm² | | Average root diameter/cm | | Root volume/cm³ | |
|---|---|---|---|---|---|---|---|---|
| | Measured value | ΔCK/% | Measured value | ΔCK/% | Measured value | ΔCK/% | Measured value | ΔCK/% |
| Control | 682.16 ± 48.71 b | - | 225.99 ± 31.55 b | - | 0.97 ± 0.09 c | - | 5.61 ± 0.73 b | - |
| Seed soaking | 879.02 ± 61.14 a | 28.86 | 338.08 ± 30.65 a | 49.60 | 1.24 ± 0.31 b | 27.84 | 10.38 ± 1.85 a | 85.03 |
| Root irrigation | 976.94 ± 70.76 a | 43.21 | 368.16 ± 28.83 a | 42.61 | 1.82 ± 0.35 a | 87.63 | 12.33 ± 2.67 a | 119.79 |
| Foliar spraying | 833.08 ± 78.59 a | 22.12 | 257.67 ± 25.81 b | 14.02 | 1.01 ± 0.13 c | 4.12 | 6.59 ± 1.32 b | 17.47 |

FIG. 3

| Treatment | Fresh weight of an underground part/g | | Fresh weight of an aboveground part/g | | Dry weight of an underground part/g | | Dry weight of an aboveground part/g | | Branch number | |
|---|---|---|---|---|---|---|---|---|---|---|
| | Measured value | ΔCK/% | Measured value | ΔCK/% | Measured value | ΔCK/% | Measured value | ΔCK/% | Measured value | ΔCK/% |
| Control | 9.91 ± 0.67 c | - | 74.68 ± 5.42 c | - | 1.58 ± 0.41 c | - | 12.03 ± 1.66 b | - | 6877 ± 554 c | - |
| Seed soaking | 15.07 ± 1.13 ab | 52.07 | 121.35 ± 11.04 a | 62.49 | 1.95 ± 0.34 b | 23.42 | 19.05 ± 2.59 a | 58.35 | 9825 ± 773 b | 42.87 |
| Root irrigation | 18.25 ± 1.29 a | 84.16 | 139.01 ± 10.86 a | 82.14 | 2.58 ± 0.29 a | 63.30 | 19.75 ± 2.68 a | 64.17 | 12410 ± 951 a | 80.46 |
| Foliar spraying | 12.42 ± 1.37 bc | 2533 | 97.58 ± 6.37 b | 30.66 | 1.68 ± 0.36 c | 6.33 | 13.77 ± 2.03 b | 14.46 | 8727 ± 602 b | 29.90 |

| Treatment | Incidence/% | Disease index | Control effect/% |
|---|---|---|---|
| Control | 91.67 ± 0.96 a | 57.74 ± 1.88 a | - |
| Seed soaking | 29.17 ± 1.59 bc | 26.95 ± 0.94 b | 53.32 ± 1.64 b |
| Root irrigation | 16.67 ± 1.36 c | 13.89 ± 0.96 c | 75.94 ± 1.67 a |
| Foliar spraying | 37.50 ± 1.83 b | 29.17 ± 1.94 b | 49.48 ± 2.27 b |

FIG. 6

| Treatment | POD/U/g·min-1 | | PPO/U/g·min-1 | | PAL/U/g·min-1 | | CAT/U/g·min-1 | |
|---|---|---|---|---|---|---|---|---|
| | Measured value | ΔCK/% | Measured value | ΔCK/% | Measured value | ΔCK/% | Measured value | ΔCK/% |
| Control | 11.29 ± 1.12 b | - | 3.28 ± 021 c | - | 4.09 ± 0.52 c | - | 13.17 ± 1.59 c | - |
| Seed soaking | 13.10 ± 0.86 a | 16 03 | 4.39 ± 0.07 b | 33.84 | 4.33 ± 0.14 c | 5.87 | 23.75 ± 327 a | 80.33 |
| Root irrigation | 14.53 ± 1.02 a | 28.70 | 5.62 ± 0.18 a | 71.34 | 6.82 ± 1.23 a | 66.75 | 27.12 ± 2.97 a | 105.92 |
| Foliar spraying | 13.59 ± 1.37 a | 20 37 | 4.58 ± 0.54 b | 39.63 | 5.42 ± 022 b | 32.52 | 16.95 ± 2.68 be | 28.7 |

FIG. 7

USE OF APPLICATION MODE OF *TRICHODERMA HARZIANUM* (*T. HARZIANUM*) IN GROWTH AND INDUCED RESISTANCE OF *NICOTIANA TABACUM* (*N. TABACUM*)

CROSS REFERENCE TO THE RELATED APPLICATIONS

This application is the national phase entry of International Application No. PCT/CN2022/143323, filed on Dec. 29, 2022, which is based upon and claims priority to Chinese Patent Application No. 202210401137.2, filed on Apr. 18, 2022, the entire contents of which are incorporated herein by reference.

TECHNICAL FIELD

The present disclosure relates to the technical field of *Nicotiana tabacum* (*N. tabacum*) growth, and in particular relates to a use of an application mode of *Trichoderma harzianum* (*T. harzianum*) in growth and induced resistance of *N. tabacum*.

BACKGROUND

*N. tabacum* is an important economic crop in China, and the long-term continuous cropping and the excessive application of fertilizers and pesticides cause problems such as declined soil quality in *N. tabacum*-growing areas, increasingly-serious disease occurrence, and decreased tobacco leaf quality, and also bring a series of negative effects to the ecological environment. Tobacco black shank (TBS) is a soil-borne fungal disease caused by *Phytophthora nicotianae* (*P. nicotianae*). TBS is common in various *N. tabacum*-growing areas in China, and in severely-affected areas, an incidence rate of TBS is higher than 75%. TBS is one of major diseases that affect the production of tobacco leaves, and heavily affects the sustainable development of production of tobacco leaves.

SUMMARY

The problem to be solved by the present disclosure is to provide a use of an application mode of *T. harzianum* in growth and induced resistance of *N. tabacum*. Different application modes of *T. harzianum* all can promote the growth of *N. tabacum* plants and reduce the occurrence of TBS, among which a root irrigation treatment at a transplanting stage leads to an optimal effect.

To achieve the above objective, the present disclosure adopts the following technical solutions:

A use of an application mode of *T. harzianum* in growth and induced resistance of *N. tabacum* is provided, including the following specific operation steps:
S1. experimental materials:
S1.1 test media:
potato dextrose agar (PDA): potato: 200 g, glucose: 20 g, agar: 15 g to 20 g, and distilled water: 1,000 mL, natural pH; and
oatmeal agar (OA): oat kernel: 60 g, sucrose: 20 g, agar: 8 g, and distilled water: 1,000 mL, natural pH; and
S1.2 preparation of bacterial solutions:
inoculating *T. harzianum* CGMCC23294 on a PDA plate, cultivating the *T. harzianum* at 27±1° C. for 5 d to 7 d, and using sterile water to rinse spores off to prepare a 1×10$^7$ cfu/mL *T. harzianum* spore suspension for later use; and inoculating *P. nicotianae* on an OA plate, cultivating the *P. nicotianae* at 26±1° C. for 6 d to 7 d, and using sterile water to rinse spores off to prepare a 1×10$^5$ cfu/mL *P. nicotianae* spore suspension for later use;
S2. experimental treatments:
in a greenhouse, collecting soil in a plough layer of a field as potting soil, removing weeds and stones from the soil, and allowing resulting soil to pass through a 1×1 cm screen mesh; and adding a compound fertilizer with m(N):m(P$_2$O$_5$):m(K$_2$O)=1:1.5:3 at 1.83 g/kg, thoroughly mixing, and placing a resulting mixture in pots that each have an inner opening diameter of 20.5 cm and a height of 13.5 cm, with 3 kg of soil per pot;
S2.1 control treatment:
subjecting *N. tabacum* seeds to surface disinfection, and sowing and cultivating disinfected *N. tabacum* seeds on a floating seedling tray filled with a sterilized substrate, with 50 plants in total;
S2.2 seed soaking treatment:
subjecting *N. tabacum* seeds to surface disinfection, and soaking disinfected seeds in the *T. harzianum* CGMCC23294 suspension for 48 h; rinsing soaked seeds with sterile water, and sowing rinsed seeds on a floating seedling tray filled with a sterilized substrate; and when *N. tabacum* seedlings reach a seedling establishment stage, transplanting the seedlings in pots, and placing the pots in a greenhouse;
S2.3 root irrigation treatment:
disinfecting *N. tabacum* seeds, and subjecting disinfected *N. tabacum* seeds to a conventional floating seedling treatment; when *N. tabacum* seedlings reach a seedling establishment stage, transplanting the seedlings in pots, with 50 plants in total; and subjecting the seedlings to a root irrigation treatment with 20 mL of the *T. harzianum* spore suspension per plant; and
S2.4 foliar inoculation treatment:
when *N. tabacum* seedlings reach a seedling establishment stage, transplanting 50 *N. tabacum* seedlings in total, and on the day of transplanting, evenly spraying 20 mL of the *T. harzianum* spore suspension on leaves of each of the *N. tabacum* seedlings until a leaf surface is covered with a layer of fine water droplets without dripping;
S3. test determination indexes and methods:
S3.1 determination of biological traits:
determination of growth indexes on day 28 after transplanting: selecting 5 plants from each treatment, determining a plant height, a stem circumference, and a leaf length and width, and calculating a leaf area of the 5th leaf from top to bottom according to a formula of leaf area=0.6345×leaf length×leaf width; pouring soil in a pot out, gently shaking off soil on a root system, rinsing repeatedly with clean water, absorbing water with absorbent paper, and measuring fresh weights of an aboveground part and an underground part; completely scanning a root system by an EPSON root scanner for imaging, storing a resulting image in a computer, and using WinRHIZO to analyze a total root length, a root surface area, an average root diameter, a root volume, and a branch number; and after the scanning is completed, deactivating the aboveground part and the underground part in a 105° C. oven for 15 min, oven-drying the aboveground part and the underground part at 70° C., and measuring dry weights of the aboveground part and the underground part and a root-shoot ratio;

S3.2 determination of physiological and biochemical indexes:

on day 7, day 14, day 21, and day 28 after transplanting, collecting 0.5 g of the fourth leaf from top to bottom in each treatment with a leaf vein avoided, and determining a chlorophyll content by an acetone-ethanol extraction colorimetric method; measuring an activity of a root system by a triphenyltetrazolium chloride (TTC) method; and determining an activity of root nitrate reductase (NR) by in vivo spectrophotometry, where 3 replicates are set for each treatment; and S3.3 determination of disease resistance and induced resistance indexes:

on day 28 after N. tabacum seedling transplanting in each treatment, evenly inoculating 20 mL of the $1\times10^5$ cfu/mL P. nicotianae spore suspension into soil around a root system of each plant through a root irrigation treatment, and 14 d later, investigating an incidence and calculating a disease index and a control effect; and collecting a root sample from an N. tabacum plant in each treatment, and determining activities of peroxidase (POD), polyphenol oxidase (PPO), phenylalanine ammonia lyase (PAL), and catalase (CAT), where 3 replicates are set for each treatment; and S4. data processing:

subjecting data to a difference significance test.

Preferably, the surface disinfection includes disinfection with 75% alcohol for 1 min and then disinfection with 30% hydrogen peroxide for 5 min.

Preferably, the root irrigation treatment with the T. harzianum spore suspension is conducted for the same time as the foliar spraying treatment; and in each of the two treatments, N. tabacum plants are transplanted simultaneously, and a transplanting mode is consistent with subsequent management measures.

The present disclosure has the following beneficial effects: The T. harzianum strain CGMCC23294 has a significant promotion effect on the biological traits and biomass accumulation of aboveground and underground parts of N. tabacum, and exhibits a better promotion effect for a leaf area than for a plant height and a stem circumference, where on the whole, a promotion effect of the root irrigation treatment>a promotion effect of the seed soaking treatment>a promotion effect of the foliar spraying treatment. On day 28 after transplanting, fresh weights of aboveground and underground parts in the root irrigation treatment group respectively increase by 84.16% and 82.12% compared with the control group; within 28 d after transplanting, the root NR activity, root activity, and leaf chlorophyll content of N. tabacum treated by the three application modes are significantly higher than those in the control group; an effect of the root irrigation treatment is better than effects of the seed soaking treatment and the foliar spraying treatment; and an incidence and a disease index of TBS in the root irrigation treatment group are significantly lower than those in the control group and other treatment groups, and the root irrigation treatment improves the activities of defensive enzymes PPO, PAL, and CAT in root cells of N. tabacum.

Different application modes of T. harzianum all can promote the growth of N. tabacum plants and reduce the occurrence of TBS, among which a root irrigation treatment at a transplanting stage leads to an optimal effect.

BRIEF DESCRIPTION OF THE DRAWINGS

FIG. 1 shows the biological traits of aboveground parts of N. tabacum plants treated with T. harzianum by different application modes in the present disclosure;

FIG. 2 shows the biological traits of underground parts of N. tabacum plants treated with T. harzianum by different application modes in the present disclosure;

FIG. 3 shows the biomass accumulation of N. tabacum plants treated with T. harzianum by different application modes in the present disclosure;

FIG. 6 shows the antagonism effects of T. harzianum applied by different application modes for TBS in the present disclosure; and FIG. 7 shows the impacts of T. harzianum applied by different application modes on induced resistance of N. tabacum in the present disclosure.

DETAILED DESCRIPTION OF THE EMBODIMENTS

Figure 4:
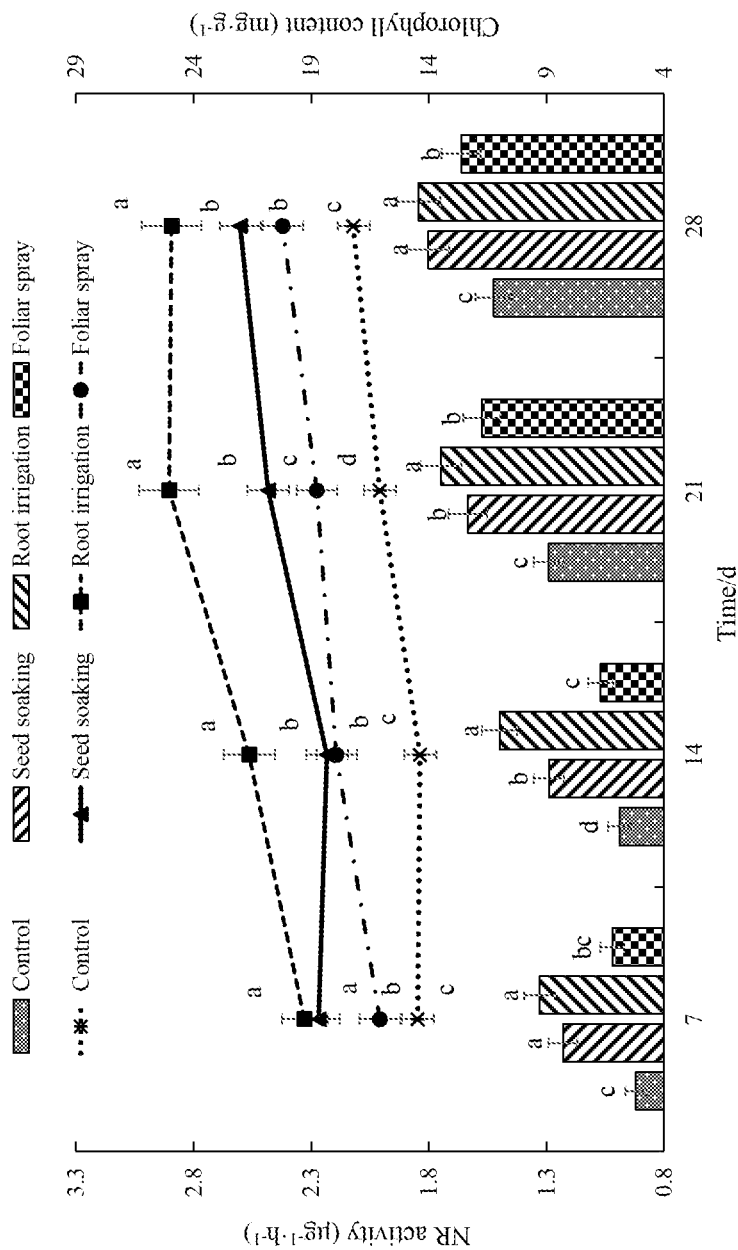
FIG. 4 is a line chart illustrating the NR activity and chlorophyll content in N. tabacum plants treated with T. harzianum by different application modes in the present disclosure.

The technical solutions of the embodiments of the present disclosure are clearly and completely described below with reference to the accompanying drawings in the embodiments of the present disclosure. Apparently, the described embodiments are merely some rather than all of the embodiments of the present disclosure. All other embodiments obtained by a person of ordinary skill in the art on the basis of the embodiments of the present disclosure without creative efforts shall fall within the protection scope of the present disclosure.

Specific embodiments are listed below.

As shown in FIG. 1 to FIG. 7, a use of an application mode of T. harzianum in growth and induced resistance of N. tabacum was provided, including the following specific operation steps:

S1. Experimental materials:

S1.1 Test media:

PDA: potato: 200 g, glucose: 20 g, agar: 15 g to 20 g, and distilled water: 1,000 mL, natural pH; and OA: oat kernel: 60 g, sucrose: 20 g, agar: 8 g, and distilled water: 1,000 mL, natural pH.

S1.2 Preparation of bacterial solutions:

T. harzianum CGMCC23294 was inoculated on a PDA plate and cultivated at 27±1° C. for 5 d to 7 d, and spores were rinsed off with sterile water to prepare a $1\times10^7$ cfu/mL T. harzianum spore suspension for later use; and P. nicotianae was inoculated on an OA plate and cultivated at 26±1° C. for 6 d to 7 d, and spores were rinsed off with sterile water to prepare a $1\times10^5$ cfu/mL P. nicotianae spore suspension for later use.

S2. Experimental treatments:

In a greenhouse, soil in a plough layer of a field was collected as potting soil, then subjected to weed and stone removal, and allowed to pass through a 1×1 cm screen mesh; and a compound fertilizer with m(N):m($P_2O_5$):m($K_2O$)=1: 1.5:3 was added at 1.83 g/kg, and a resulting mixture was thoroughly mixed and placed in pots that each had an inner opening diameter of 20.5 cm and a height of 13.5 cm, with 3 kg of soil per pot.

S2.1 Control treatment:

N. tabacum seeds were subjected to surface disinfection, and then sown and cultivated on a floating seedling tray filled with a sterilized substrate, with 50 plants in total, where the surface disinfection included disinfection with 75% alcohol for 1 min and then disinfection with 30% hydrogen peroxide for 5 min.

S2.2 Seed soaking treatment:

*N. tabacum* seeds were subjected to surface disinfection, then soaked in the *T. harzianum* CGMCC23294 suspension for 48 h, then rinsed with sterile water, and sown on a floating seedling tray filled with a sterilized substrate; and when *N. tabacum* seedlings reached a seedling establishment stage, the seedlings were transplanted into pots, and the pots were placed in a greenhouse.

S2.3 Root irrigation treatment:

*N. tabacum* seeds were disinfected and then subjected to a conventional floating seedling treatment; when *N. tabacum* seedlings reached a seedling establishment stage, the seedlings were transplanted into pots, with 50 plants in total; and the seedlings were subjected to a root irrigation treatment with 20 mL of the *T. harzianum* spore suspension per plant.

S2.4 Foliar inoculation treatment:

When *N. tabacum* seedlings reached a seedling establishment stage, 50 *N. tabacum* seedlings were transplanted in total, and on the day of transplanting, 20 mL of the *T. harzianum* spore suspension was evenly sprayed on leaves of each of the *N. tabacum* seedlings until a leaf surface was covered with a layer of fine water droplets without dripping.

The root irrigation treatment with the *T. harzianum* spore suspension was conducted for the same time as the foliar spraying treatment; and in each of the two treatments, *N. tabacum* plants were transplanted simultaneously, and a transplanting mode was consistent with subsequent management measures.

S3. Test determination indexes and methods:

S3.1 Determination of biological traits:

Determination of growth indexes on day 28 after transplanting: 5 plants were selected from each treatment, a plant height, a stem circumference, and a leaf length and width were determined, and a leaf area of the 5th leaf from top to bottom was calculated according to a formula of leaf area=0.6345×leaf length×leaf width; soil in a pot was poured out, soil on a root system was gently shaken off, a plant was rinsed repeatedly with clean water, residual water was absorbed with absorbent paper, and fresh weights of an aboveground part and an underground part were measured; a root system was completely scanned by an EPSON root scanner for imaging, a resulting image was stored in a computer, and WinRHIZO was used to analyze a total root length, a root surface area, an average root diameter, a root volume, and a branch number; and after the scanning was completed, the aboveground part and the underground part were deactivated in a 105° C. oven for 15 min and then oven-dried at 70° C., and dry weights of the aboveground part and the underground part and a root-shoot ratio were measured.

S3.2 Determination of physiological and biochemical indexes:

On day 7, day 14, day 21, and day 28 after transplanting, 0.5 g of the fourth leaf from top to bottom was collected in each treatment with a leaf vein avoided, and a chlorophyll content was determined by an acetone-ethanol extraction colorimetric method; an activity of a root system was measured by a TTC method; and an activity of root NR was determined by in vivo spectrophotometry, where 3 replicates were set for each treatment.

S3.3 Determination of disease resistance and induced resistance indexes:

On day 28 after *N. tabacum* seedling transplanting in each treatment, evenly inoculating 20 mL of the 1×10$^5$ cfu/mL *P. nicotianae* spore suspension into soil around a root system of each plant through a root irrigation treatment, and 14 d later, investigating an incidence and calculating a disease index and a control effect; and a root sample was collected from an *N. tabacum* plant in each treatment, and activities of POD, PPO, PAL, and CAT were determined, where 3 replicates were set for each treatment;

incidence=[number of diseased plants/total number of surveyed plants]×100;

disease index=Σ(disease grade×number of plants at this disease grade)/(highest disease grade×total number of surveyed plants)×100;

and control effect (%)=(number of non-diseased plants/ total number of surveyed plants)×100.

S4. Data processing:

Data were subjected to a difference significance test.

1. Impacts of *T. harzianum* Applied by Different Application Modes on Biological Traits 1.1 Impacts on Biological Traits of an Aboveground Part of *N. tabacum*

It can be seen from FIG. 1 that, 28 d after transplanting, the treatment with *T. harzianum* by the three application modes has a significant promotion effect on the growth of an aboveground part of *N. tabacum* compared with the control, where the root irrigation treatment has the most significant improvement effect for a plant height and leaf area of *N. tabacum*, and increases the plant height and leaf area respectively by 54.21% and 67.42% with P<0.05, which are significantly higher than that of the seed soaking and foliar spraying treatments; and compared with the blank control, the three application modes have a significant impact on an increase of a stem circumference, where the foliar spraying treatment leads to an increase as high as 23.40%, P<0.05.

Overall, *T. harzianum* exhibits a better promotion effect for a leaf area and a plant height of *N. tabacum* than for a stem circumference, that is, a promotion effect for a leaf area>a promotion effect for a plant height>a promotion effect for a stem circumference.

1.2 Impacts on Biological Traits of an Underground Part of *N. tabacum*

It can be seen from FIG. 2 that the three application modes have different degrees of promotion effects for various indexes of a root system of *N. tabacum*; on day 28 after transplanting, *N. tabacum* treated with *T. harzianum* through root irrigation has a developed root system and has root indexes higher than those of the seed soaking and foliar spraying treatments, and the average root diameter, root volume, and branch number of *N. tabacum* treated with *T. harzianum* through root irrigation increase significantly compared with the blank control, with increases respectively of 87.63%, 119.79%, and 80.46% (P<0.05); the root surface area and root volume of *N. tabacum* treated through seed soaking increase significantly, with increases respectively of 49.60% and 85.03% (P<0.05), which are similar to effects of the root irrigation treatment; the foliar spraying treatment has no significant impact on the root surface area, average root diameter, and root volume of *N. tabacum* compared with the blank control, with increases respectively of 14.02%, 4.12%, and 17.47% (P<0.05); and impacts of the three application modes of *T. harzianum* on biological traits of an aboveground part and an underground part of *N. tabacum* are as follows: an impact of the root irrigation treatment>an impact of the seed soaking treatment>an impact of the foliar spraying treatment.

1.3 Impacts on the Biomass Accumulation of *N. tabacum*

It can be seen from FIG. 3 that the biomass accumulation in an aboveground part and an underground part of *N. tabacum* treated with *T. harzianum* through seed soaking, root irrigation, and foliar spraying is significantly higher than that in the blank group, where a promotion effect of the root irrigation treatment>a promotion effect of the seed soaking treatment>a promotion effect of the foliar spraying treatment; fresh weights and dry weights of an aboveground part and an underground part of *N. tabacum* treated with *T. harzianum* through root irrigation increase by 84.16%, 82.12%, 63.29%, and 64.17% respectively compared with the control (P<0.05); a fresh weight and a dry weight of an aboveground part of *N. tabacum* treated with *T. harzianum* through seed soaking increase significantly by 62.49% and 58.35% respectively (P<0.05), which are not significantly different from the root irrigation treatment; and there is no significant difference in a root-shoot ratio of *N. tabacum* among the control, the seed soaking treatment, and the root irrigation treatment, and a root-shoot ratio of *N. tabacum* treated with *T. harzianum* through foliar spraying decreases, indicating that *T. harzianum* can promote the biomass accumulation in aboveground and underground parts of *N. tabacum*.

2. Impacts of *T. harzianum* Applied by Different Application Modes on Physiological Characteristics 2.1 Impacts on the Root NR Activity and Leaf Chlorophyll Content in *N. tabacum*

It can be seen from FIG. 4 that a chlorophyll content gradually increases over time after transplanting, and a chlorophyll content at each stage is as follows: a chlorophyll content in the root irrigation treatment>a chlorophyll content in the seed soaking treatment>a chlorophyll content in the foliar spraying treatment>a chlorophyll content in the control; chlorophyll contents of the seed soaking treatment and the root irrigation treatment at each stage are significantly different from that of the blank, with maximum increases of 33.70% and 51.52%, respectively (P<0.05), which appear on day 7 and day 14 after transplanting, respectively; on day 28 after transplanting, there is no significant difference between the seed soaking treatment and the root irrigation treatment;

on day 14 after transplanting, there is no significant difference between the foliar spraying treatment and the blank treatment; and on day 21 after transplanting, a chlorophyll content of the foliar spraying treatment is 21.61% higher than a chlorophyll content of the control (P<0.05).

The root NR activities of *N. tabacum* treated with *T. harzianum* by the three application modes at each stage are significantly different from that of the control; an overall change trend of the root NR activity is the same as that of chlorophyll, that is, the root NR activity gradually increases over time after transplanting; the root NR activity of *N. tabacum* treated with *T. harzianum* through root irrigation is always at a high level, and on day 21 after transplanting, the seed soaking treatment and the root irrigation treatment lead to maximum increases of 29.54% and 55.72%, respectively (P<0.05); on day 14 after transplanting, the foliar spraying treatment is most significantly different from the blank control, with an increase of 24.77% (P<0.05); and on day 28 after transplanting, the root irrigation treatment leads to the highest root NR activity of *N. tabacum*, and there is no significant difference between the seed soaking treatment and the foliar spraying treatment.

2.2 Impacts on the Root Activity of *N. tabacum*

Figure 5:
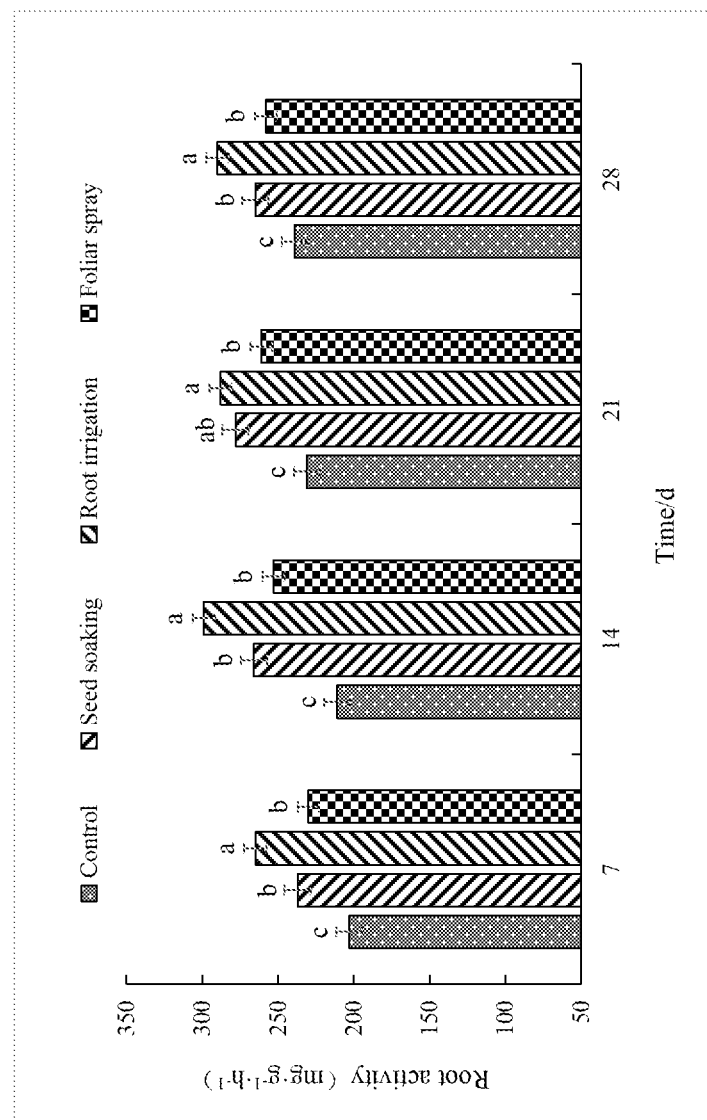
FIG. 5 is a histogram illustrating root activities of N. tabacum plants treated with T. harzianum by different application modes in the present disclosure.

It can be seen from FIG. 5 that the *T. harzianum* treatment can improve the root activity of *N. tabacum* to different degrees; the root activities of *N. tabacum* treated with *T. harzianum* by the three application modes increase over time after transplanting, with a trend of first increasing and then decreasing; the root irrigation treatment leads to the strongest promotion effect, and a peak value of the promotion effect occurs on day 14 after transplanting, indicating the largest increase of 41.71% compared with the blank control (P<0.05); peak values of root activities of *N. tabacum* in the seed soaking treatment and the foliar spraying treatment appear on day 21 after transplanting, and increase by 20.35% and 12.99% respectively compared with the blank (P<0.05); the root activity of the blank treatment gradually increases, and a difference between the blank treatment and each treatment decreases over time after transplanting, but on day 28 after transplanting, the root activity of the blank treatment is still significantly lower than that of the *T. harzianum* treatment.

2.3 Impacts of *T. harzianum* Applied by Different Application Modes on Induced Resistance of *N. tabacum*

2.3.1 Impacts on an Antagonism Effect for TBS

The incidence and disease index in the blank treatment are significantly higher than those in the *T. harzianum* treatment; the root irrigation treatment leads to the most significant control effect of 75.94% for TBS and reduces a disease index from 57.74 to 13.89 (P<0.05); and the *T. harzianum* treatments through seed soaking and foliar spraying are not significant from each other in the incidence, disease index, and control effect of TBS, and lead to control effects of 53.32% and 49.48%, respectively (P<0.05).

2.3.2 Impacts on Induced Resistance of *N. tabacum*

The induced resistance is usually reflected by activities of the defensive enzymes POD, PPO, PAL, and CAT, and it can be seen from FIG. 7 that *T. harzianum* has an inductive effect for the activities of the four defensive enzymes.

POD activity: The three application modes all can effectively increase an activity of root POD of *N. tabacum*, but there is no significant difference among the three; and a POD activity of *N. tabacum* in the root irrigation treatment increases by 28.70% (P<0.05) compared with the control, which is slightly higher than that of the seed soaking and foliar spraying treatments.

PPO activity: The root irrigation treatment leads to the most significant improvement effect, and can increase the PPO activity by 71.34% compared with the blank (P<0.05); and there is no significant difference between the seed soaking treatment and the foliar spraying treatment, and the two treatments increase the PPO activity by 33.84% and 39.63%, respectively (P<0.05).

PAL activity: An activity of root PAL of *N. tabacum* in the seed soaking treatment increases by 5.87% compared with the blank (P<0.05), with no significant difference from the blank; and compared with the blank, the root irrigation and foliar spraying treatments can significantly increase the PAL activity by 66.75% and 32.52%, respectively (P<0.05).

CAT activity: The seed soaking and root irrigation treatments lead to the most significant improvement effects of 80.33% and 105.92% for the CAT activity, respectively (P<0.05); and the foliar spraying treatment has a significantly-lower improvement effect than the seed soaking and root irrigation treatments, and the foliar spraying treatment only increases the CAT activity by 28.7% (P<0.05), with no significant difference from the blank.

In summary, the three application modes can promote the activities of POD, PPO, PAL, and CAT in a root system of *N. tabacum*, among which the root irrigation treatment leads to the most significant improvement effect for the activity of each of the defensive enzymes. The POD activity is less affected by an application mode of *T. harzianum*, and the PAL and CAT activities are most affected by an application mode of *T. harzianum*. Under a biological stress, the root irrigation treatment is beneficial to stimulation of POD, PPO, PAL, and CAT activities in a root system of *N. tabacum*, thereby improving the induced resistance of *N. tabacum*.

Investigation results of the present disclosure show that the overall promotion effects of the three application modes for various physiological indexes of *N. tabacum* are as follows: a promotion effect of the root irrigation treatment>a promotion effect of the seed soaking treatment>a promotion effect of the foliar spraying treatment; and the root irrigation treatment can increase a chlorophyll content in leaves of *N. tabacum*, accelerate a photosynthetic rate of leaves of *N. tabacum*, enhance the formation and accumulation of carbohydrates in *N. tabacum*, increase the root activity and NR activity of *N. tabacum*, and improve the water and fertilizer absorption and nitrogen use efficiency in soil to promote the plant height, leaf area, root volume expansion, and biomass accumulation of *N. tabacum*, which is also one of the mechanisms of *T. harzianum* to promote the growth of a plant.

The plant-*T. harzianum*-pathogen interaction is a complicated system, and plays a vital role in resistance induction during a disease-resistant process of a plant, which means that, under the induction of an external factor, a plant activates its own defense system, including synthesis of various physiological and biochemical factors such as defensive enzymes, lignin, phytoalexin, and disease-associated proteins and enhancement of resistance to pathogens.

POD and CAT are the major enzymes responsible for scavenging reactive oxygen species (ROS) in a plant, and POD can induce the synthesis of lignin. As a key enzyme in the synthesis of phytoalexin, PAL, together with PPO, participates in the oxidation of phenols into quinones with high antibacterial activities. A large number of studies have shown that *T. harzianum* can induce the increase of activities of defensive enzymes such as POD, CAT, PPO, and PAL in a plant to resist the invasion of pathogens and effectively reduce the occurrence of a disease. Under a stress of *P. nicotianae*, a root system of *N. tabacum* treated with *T. harzianum* through root irrigation has the highest defensive enzyme activities, and compared with the control, the POD, PPO, PAL, and CAT activities increase by 28.70%, 71.34%, 66.75%, and 105.92%, respectively; and the root irrigation treatment leads to a control effect of 75.94% for TBS, which is significantly higher than that of other treatments.

The control effect for TBS increases with the increase of activities of defensive enzymes in *N. tabacum*, indicating that the induction of *T. harzianum* can improve the activities of resistance-associated enzymes in *N. tabacum*, thereby producing quinones, lignin, phytoalexin, or the like to prevent the infection of pathogens and enhance the disease resistance of *N. tabacum*. Therefore, the resistance induction is an important mechanism for control of TBS by *T. harzianum* CGMCC23294.

The above are merely preferred specific embodiments of the present disclosure, but the protection scope of the present disclosure is not limited thereto. Any equivalent replacement or modification made by a person skilled in the art according to the technical solutions of the present disclosure and inventive concepts thereof within the technical scope of the present disclosure shall fall within the protection scope of the present disclosure.

What is claimed is:

1. A method of growing and inducing resistance of *Nicotiana tabacum* (*N. tabacum*), comprising the following specific operation steps:
   S1. experimental materials:
   S1.1 test media:
   a potato dextrose agar (PDA): potato: 200 g, glucose: 20 g, agar: 15 g to 20 g, and distilled water: 1,000 mL; and
   an oatmeal agar (OA): oat kernel: 60 g, sucrose: 20 g, agar: 8 g, and distilled water: 1,000 mL; and
   S1.2 preparation of bacterial solutions:
   inoculating *Trichoderma harzianum* (*T. harzianum*) (CGMCC23294) on a PDA plate, cultivating the *T. harzianum* at 27±1° C. for 5 d to 7 d, and using sterile water to rinse spores from the *T. harzianum* off to prepare a $1\times10^7$ cfu/mL *T. harzianum* spore suspension for later use; and inoculating *Phytophthora nicotianae* (*P. nicotianae*) on an OA plate, cultivating the *P. nicotianae* at 26±1° C. for 6 d to 7 d, and using sterile water to rinse spores from the *P. nicotianae* off to prepare a $1\times10^5$ cfu/mL *P. nicotianae* spore suspension for later use;
   S2. experimental treatments:
   in a greenhouse, collecting a soil in a plough layer of a field as a potting soil, removing weeds and stones from the potting soil, and allowing a resulting soil to pass through a 1×1 cm screen mesh; and adding a compound fertilizer with $m(N):m(P_2O_5):m(K_2O)=1:1.5:3$ at 1.83 g/kg, mixing, and placing a resulting mixture in pots to obtain a resulting potting soil, wherein each of the pots has an inner opening diameter of 20.5 cm and a height of 13.5 cm, 3 kg of the resulting potting soil is placed per pot;
   S2.1 a control treatment:
   subjecting first *N. tabacum* seeds to a surface disinfection to obtain first disinfected *N. tabacum* seeds, and sowing and cultivating the first disinfected *N. tabacum* seeds for 50 plants on a first floating seedling tray;
   S2.2 a seed soaking treatment:
   subjecting second *N. tabacum* seeds to the surface disinfection to obtain second disinfected *N. tabacum* seeds, and soaking the second disinfected *N. tabacum* seeds in the *T. harzianum* spore suspension for 48 h to obtain soaked seeds; rinsing the soaked seeds with sterile water to obtain rinsed seeds, and sowing the rinsed seeds on a second floating seedling tray to obtain first *N. tabacum* seedlings; and when the first *N. tabacum* seedlings reach a seedling establishment stage, transplanting the first *N. tabacum* seedlings in the pots to obtain first resulting pots, and placing the first resulting pots in the greenhouse;
   S2.3 a root irrigation treatment:
   disinfecting third *N. tabacum* seeds to obtain third disinfected *N. tabacum* seeds, and subjecting the third disinfected *N. tabacum* seeds to a conventional floating seedling treatment to obtain second *N. tabacum* seedlings; when the second *N. tabacum* seedlings reach the seedling establishment stage, transplanting the second *N. tabacum* seedlings in the pots, with 50 plants in total; and subjecting the second *N. tabacum* seedlings to the root irrigation treatment with 20 mL of the *T. harzianum* spore suspension per plant; and
   S2.4 a foliar inoculation treatment:
   when the second *N. tabacum* seedlings reach the seedling establishment stage, transplanting the 50 second *N. tabacum* seedlings, and on a day of the transplanting, evenly spraying 20 mL of the *T. harzianum* spore suspension on leaves of each of the 50 second *N. tabacum* seedlings until a leaf surface is covered with a layer of fine water droplets without dripping;

S3. test determination indices and methods:

S3.1 a determination of biological traits:

a determination of growth indices on day 28 after the transplanting: selecting 5 plants from each treatment, determining a plant height, a stem circumference, and a leaf length and a leaf width, and calculating a leaf area of a 5th leaf from a top to a bottom of each plant according to a formula of leaf area=0.6345×leaf length×leaf width, wherein the 5th leaf is the leaf that is counted starting from the top of the plant and proceeding towards the bottom of the plant; pouring the resulting potting soil in the pots out, gently shaking off a soil on a root system, rinsing with clean water, absorbing the water used for rinsing with an absorbent paper, and measuring fresh weights of the aboveground part of the plant and the underground part of the plant; completely scanning the root system by a root scanner for imaging, storing a resulting image in a computer, and using an image analysis system to analyze a total root length, a root surface area, an average root diameter, a root volume, and a branch number; and after the scanning is completed, deactivating the aboveground part and the underground part in a 105° C. oven for 15 min, oven-drying the aboveground part and the underground part at 70° C. to obtain a resulting aboveground part and a resulting underground part, and measuring dry weights of the resulting aboveground part and the resulting underground part and a root-shoot ratio;

S3.2 a determination of physiological and biochemical indexes:

on day 7, day 14, day 21, and day 28 after the transplanting, collecting 0.5 g of a fourth leaf from the top to the bottom in each treatment with a leaf vein avoided, wherein the fourth leaf is the leaf that is counted starting from the top of the plant and proceeding towards the bottom of the plant, and determining a chlorophyll content by an acetone-ethanol extraction colorimetric method; measuring an activity of the root system by a triphenyltetrazolium chloride (TTC) method; and determining an activity of a root nitrate reductase (NR) by in vivo spectrophotometry, wherein 3 replicates are set for each treatment; and S3.3 a determination of disease resistance and induced resistance indexes:

on day 28 after the transplanting in each treatment, evenly inoculating 20 mL of the $1\times10^5$ cfu/mL *P. nicotianae* spore suspension into the soil around the root system of each plant through the root irrigation treatment, and 14 days later, investigating an incidence of each treatment and calculating a disease index and a control effect of each treatment; and collecting a root sample from an *N. tabacum* plant in each treatment, and determining activities of a peroxidase (POD), a polyphenol oxidase (PPO), a phenylalanine ammonia lyase (PAL), and a catalase (CAT), wherein 3 replicates are set for each treatment; and S4. data processing:

subjecting data to a difference significance test.

2. The resistance method of growing and inducing of the *N. tabacum* according to claim 1, wherein the surface disinfection comprises a disinfection with 75% alcohol for 1 min and then a disinfection with 30% hydrogen peroxide for 5 min.

3. The resistance method of growing and inducing of the *N. tabacum* according to claim 1, wherein the root irrigation treatment with the *T. harzianum* spore suspension is conducted for a same time as the foliar inoculation treatment; and in each of the root irrigation treatment and the foliar inoculation treatment, *N. tabacum* plants are transplanted simultaneously.

* * * * *